United States Patent [19]

Whitaker

[11] Patent Number: 5,177,306
[45] Date of Patent: Jan. 5, 1993

[54] ABIENOL-PRODUCING SOMACLONAL VARIANTS OF NICOTIANA

[75] Inventor: Robert J. Whitaker, Burlington, N.J.

[73] Assignees: DNA Plant Technology Corporation, Cinnaminson, N.J.; Firmenich S.A., Geneva, Switzerland

[21] Appl. No.: 405,698

[22] Filed: Sep. 11, 1989

Related U.S. Application Data

[63] Continuation-in-part of Ser. No. 256,515, Oct. 12, 1988, Pat. No. 5,012,040.

[51] Int. Cl.$^5$ .......................... A01H 4/00; C12N 5/04
[52] U.S. Cl. ................................ 800/200; 800/230; 800/DIG. 40; 800/DIG. 43; 435/240.49
[58] Field of Search .......... 800/1, 200, 230, DIG. 43, 800/DIG. 40; 47/58; 568/819; 435/240.49

[56] References Cited

U.S. PATENT DOCUMENTS

| | | | |
|---|---|---|---|
| 3,060,172 | 10/1962 | Teague et al. | 260/236 |
| 4,818,649 | 4/1989 | Evans et al. | 435/240.49 |
| 4,857,465 | 8/1989 | Barwale et al. | 435/240.49 |

OTHER PUBLICATIONS

Whitaker et al (1986) in Evans et al. *Handbook of Plant Cell Culture*, MacMillan Publishing Co., N.Y., pp. 264-286.
Chaleff (1983) Science 219: 676-682.
Tomita et al (1980) Agric. Biol. Chem. 44: 2517-2518.
C. E. Flick et al., in: *Handbook of Plant Cell Culture*, 2 (Chapter 21):606-630, W. R. Sharp et al. (ed) MacMillian Publishing Co., New York (1984).
H. Tomita et al., Agric. Biol. Chem., 44(10):2517-2518 (1980).
D. A. Evans et al., American Journal of Botany, 71(6):759-774 (1984).
B. Reisch, in: *Handbook of Plant Cell Culture*, 1 (Chapter 25):748-769, Evans et al. (ed), MacMillan Publishing Co., New York (1983).
J. A. Bailey et al., J. Gen. Microbiol., 85:57-64 (1974).
T. Kubo et al., Tobacco Science Yearbook, 26:126-128 (1982).
Leffingwell et al., in: *Recent Advances in Tobacco Science*, 14:169-218 (1988).
Ogino et al., Phytochemistry, 17:1907-1910 (1978).

*Primary Examiner*—Elizabeth C. Weimar
*Assistant Examiner*—Che Chereskin
*Attorney, Agent, or Firm*—Pennie & Edmonds

[57] ABSTRACT

The present invention provides a method for producing plants with labdane production in Nicotiana which comprises subjecting plans to somaclonal variation, and screening for plants having higher than average labdane content. The invention also provides improved *Nicotiana sp.* plant lines producing at least about 800 mg of cis-abienol or sclareol per kg of fresh plant weight.

19 Claims, 5 Drawing Sheets

ABIENOL-PRODUCING SOMACLONAL VARIANTS OF NICOTIANA

RELATED APPLICATIONS

This application is a continuation-in-part of U.S. Ser. No. 265,515, filed Oct. 12, 1988, which issued as U.S. Pat. No. 5,012,040 on Apr. 30, 1991.

TABLE OF CONTENTS

1. Introduction
2. Background of the Invention
   2.1. Sclareol
   2.2. Cis-Abienol
3. Summary of the Invention
4. Brief Description of the Figures
5. Detailed Description of the Invention
   5.1. Obtaining Somaclonal Variants
   5.2. Screening for Variants
     5 2.1 High Sclareol-Producing Somaclones
     5.2.2. High Cis-Abienol Producing Somaclones
6. Examples
   6.1. Inducing Somaclonal Variation
   6.2. Screening for Labdane Production
   6.3. $R_2$ Generation
   6.4. Somaclone Hybrids

1. INTRODUCTION

The present invention relates to novel plants producing unusually high levels of labdanes. More specifically, the invention relates to somaclonal variants of Nicotiana which exhibit a several-fold increase in the production of compounds such as sclareol and cis-abienol, relative to the naturally occurring plant. The availability of these novel plant lines produces a convenient, reliable source of these compounds, which can be produced in commercial quantities.

2. BACKGROUND OF THE INVENTION

2.1. Sclareol

The labdane diterpene sclareol (labd-14-ene-8,13-diol) is a compound of substantial value to the fragrance industry. Sclareol and related derivatives are noted as starting materials in perfume manufacture, and also to enhance the flavor of tobacco (U.S. Pat. No. 4,441,514). The compound is found in nature in many plant sources, among these including *Rhabdodendron macrophyllum*, Filho et al., *Phytochemistry*, Vol. 24, No. 9, pp. 1991–1993 (1985); *Salvia palestina*, Ulubelin et al., *Phytochemistry*, Vol. 24. No. 6, pp. 1386–1387 (1985); *Stevia monardaefolia*, Quijano et al., *Phytochemistry*, Vol. 21 No. 6, pp. 1369–1371 (1985) Nicotiana glutinosa (Bailey et al. *J. Gen. Microbiol.* 85:57–84, 1974), and *Salvia sclarea* (U.S. Pat. No. 3,060,172). The latter species, also known as clary sage, represents the primary commercial source of sclareol at the present time. The sclareol produced by *S. sclarea* occurs in the flower stalks in the epidermal appendages or hairs known as trichomes. Although the concentration of sclareol in these hairs is relatively high, this is the only location on the plant where sclareol is produced; there is little or no sclareol present in the leaf, root or stems of clary sage. Thus, the quantities of sclareol that can be derived from this plant are relatively limited. To further complicate matters, clary sage flower stalks are sensitive to rain, so that, under routine environmental conditions, the normal yield of sclareol may be even further reduced.

An alternate source of sclareol would clearly be desirable, but to date none of the other known botanic producers of sclareol has been found to be a suitable substitute for clary sage. It has recently been discovered, however, that *Nicotiana glutinosa* produces sclareol in leaves, stems and flower stalks. *N. glutinosa* has never been produced in commercial quantities, however and the overall amounts produced are still relatively small. Nonetheless, the extensive distribution of sclareol in the plant and its relative hardiness makes *N. glutinosa* a valuable candidate for replacement and/or supplement of clary sage, if sclareol production could be increased. One possible means by which this could possibly be achieved is somaclonal variation.

2.2. Cis-Abienol

The leaves of commercial tobacco, *Nicotiana tabacum* are known to be covered by a gummy exudate, or cuticular wax; this material is apparently produced by trichomes, or leaf hairs, on the plant's surface. The chemical composition of this cuticular component has been the subject of investigation by many workers (e.g., see Severson et al. *J. Agric. Food Chem.* 32:566–570, 1984). The majority of compounds isolated and identified from the cuticular waxes are diterpenes and long chain ($C_{25}$–$C_{36}$) aliphatic hydrocarbons. It is generally believed that one or more of the components of this exudate, particularly the diterpenoid components, upon degradation during curing and aging give rise to volatile terpenes which may favorably affect the flavor of tobacco.

The distribution of the various types of diterpenes is not consistent throughout the numerous known cultivars of tobacco. Depending on the genetic background of a particular line, it may be particularly high in duvane diterpenes, or it may be high in labdanes. The major duvanes found on the leaves of commercially produced American tobacco are $\alpha + \beta$-4,8,13-duvatriene-1,3-diols; the principal diterpenes found on labdane producing plants are (12Z)-labda-12,14-diene-8α-ol (cis-abienol) and (13ε)labda-13-ene-8α,15-diol. These compounds are probably precursors to numerous minor labdanoic components also found in cuticular waxes.

As noted above, the presence of labdanoids is apparently associated with a certain aroma and flavor in tobacco. Particular interest has been shown in determining the genetics and mode of inheritance of the ability to produce cis-abienol (Tomita et al., *Agric. Biol. Chem.* 44:2517–2518, 1980; Kubo et al., *Tob. Sci.* XXVI:1-26–128, 1982). Surveys of a large number of varieties suggests that a very small proportion, perhaps no more than one quarter, produce significant quantities of cis-abienol. The presence of abienol has a desirable effect on flavor of tobacco, probably due to the degradation products derived from it during the tobacco curing process. It is also useful in the fragrance industry as a substrate for chemical conversion to ambrox a component or substrate of ambergris compounds. Thus, efforts have been focused on how to confer the cis-abienol producing trait, or enhance cis-abienol production in existing labdane-producing lines. Traditional breeding methods have failed to yield any significant advances in this regard, and all existing tobacco lines still produce fairly low levels of cis-abienol. There is also no convenient synthetic source of the compound. The technique of somaclonal variation, however, can provide an effective alternative to traditional breeding methods in crop improvement.

SOMACLONAL VARIATION

Methods of plant tissue culture have now been used for years as a means of asexual reproduction, enabling a more rapid rate of propagation than is available with traditional vegetative propagation. It is of course expected that the regenerated plants will be exact copies of the plant from which the tissue explant was taken. Early in the history of plant tissue culture, it was noticed that phenotypic variants commonly occurred among regenerated plants. These anomalies were typically dismissed as artifacts of tissue culture, representing "epigenetic" events which were of no value scientifically, except as a curiosity.

It has been more recently recognized that the appearance of such variants is a relatively regular occurrence in certain plants, and this provides a potentially valuable source of genetic variability for use in crop improvement (Larkin and Scowcroft, *Theor. Appl. Genet* 60:197-214, 1981: Evans et al., *Amer. J. Bot.* 71:759-774, 1984). The resulting variants are now referred to as somaclonal variants or somaclones and have been observed in a number of different plant species, including tobacco.

A number of different techniques have been used to induce or favor the production of somaclonal variants (Reisch, "Genetic Viability in Regenerated Plants", in *Handbook of Plant Cell Culture*, Vol. 1. Chap. 25, 1983, McMillan Publishing). Among the manipulations which may be used to encourage variation are long-term culture cycles, protoplast culture cycles, callus culture cycles, explants from specific tissue types, growth on a specific nutrient medium or hormone formulation, or the use of specific genotypes known to produce increased amounts of variations. These techniques are not mutually exclusive, and one or more may be combined to achieve the desired level of variation.

The techniques described above have not proven to be unusually applicable to all plants, however. Some species may readily produce somaclonal variants in, for example, a protoplast culture cycle, while other species. even within the same genus, will not. Similarly, there is no way to predict, a priori, the nature of the somaclones which will be produced, until the conditions which induce variation for a particular species have been determined. In essence, unless the species in question has previously been shown to produce somaclones, with any degree of certainty, it is impossible to know whether somaclones will be produced, and for what type of characteristics variation will be observed.

SOMACLONAL VARIATION IN NICOTIANA

Isolation of in vitro mutants from cultured *Nicotiana sp.* has been reported by many workers (See, Flick and Evans, "Tobacco" in *Handbook of Plant Cell Culture*; Vol. 2, Chap. 21, Table 5, 1984; Barbier and Dulieri *Ann. Amelior. Plant.* 30:321-344, 1980. Most of these mutants have been isolated from N. tabacum, cultivated tobacco. The majority of those reported have been specifically selected for resistance to an antimetabolite, such as antibiotics, fungicides and herbicides. Other wild species of Nicotiana, specifically *N. sylvestris* and *N. plumbaginifolia* have also been shown to produce mutants in vitro. However there has not previously been any demonstration, or indeed any attempt, to produce somaclones from *N. glutinosa*.

The present invention has now identified a means for producing somaclonal variants, and regenerated plants therefrom, in species of Nicotiana; more importantly, however, among the somaclonal variants produced are a number of lines which produce much higher than average levels of labdanes. Lines such as these have been repeatedly and reliably obtained from both *N. glutinosa* and *N. tabacum* somaclonal variation programs, and thus represent a novel and valuable source for the production of commercial quantities of important labdanes.

3. SUMMARY OF THE INVENTION

The invention provides a method of producing Nicotiana lines having above average labdane content which comprises culturing an explant of young tissue of Nicotiana on a nutrient medium containing at least one cytokinin at a concentration of about 5-20 uM for a period of time sufficient to obtain a callus; regenerating plants from said callus; and screening the regenerated plants for variants producing higher than average levels of labdane.

In one embodiment, the present invention provides novel lines of the species *Nicotiana glutinosa* which produce unusually high levels of the labdane diterpene sclareol. Specifically, these novel lines produce at least about 800 mg sclareol/kg of fresh plant material and typically at least about 1000 mg/kg or more of plant material. This represents at least up to a 2- to 3-fold increase in sclareol production over unmodified *N. glutinosa*, which normally yields a maximum of about 300-600 mg/kg. The use of these improved *N. glutinosa* lines also provides an advantage over the traditional method of obtaining sclareol from clary sage. Although clary sage can produce large quantities of sclareol, the level of production tends to be extremely variable. For example, yield for clary sage can be anywhere from 2-31 kg/acre. This compares with 7-10 kg/acre for unmodified *N. glutinosa* somaclones. Also, clary sage requires a growing period of about 18 months before sclareol can be obtained in significant quantities. Therefore, the present somaclone lines provide a more reliable and convenient source of sclareol than traditional sources.

In a second embodiment the present invention provides novel lines of *Nicotiana tabacum* which produce unusually high levels of the labdane cis-abienol. Specifically, these novel plant lines produce more than about 800 mg of cis-abienol/kg of fresh plant material, preferably at least about 1000 mg/kg, and most preferably at least about 1200 to about 1600 mg/kg or more of fresh plant material. In a preferred embodiment, this represents a 4 to 8-fold increase in cis-abienol production over unmodified *N. tabacum*, which normally produces no abienol, but when abienol is present, generally produce a maximum of about 200 mg/kg. The use of these improved *N. tabacum* lines provides a convenient source of the compound cis-abienol, which has heretofore been impossible to produce in commercial quantities, either from natural or synthetic sources.

These modified lines also provide the basis for the production of hybrid lines. utilizing as one or both parents, the novel lines of the present invention. Also within the scope of the present invention are clones, somaclones, gametoclones and mutants of the novel lines.

4. BRIEF DESCRIPTION OF THE FIGURES

FIG. 1 presents a summary of the pattern of sclareol production in somaclones of the DE line of *Nicotiana glutinosa*.

FIG. 2 presents a summary of the pattern of sclareol production in somaclones of the VS line of *Nicotiana glutinosa*.

FIG. 4A shows the distribution of abienol from R2 somaclones upon bulk analysis of replicate 1.

Figure 4A:
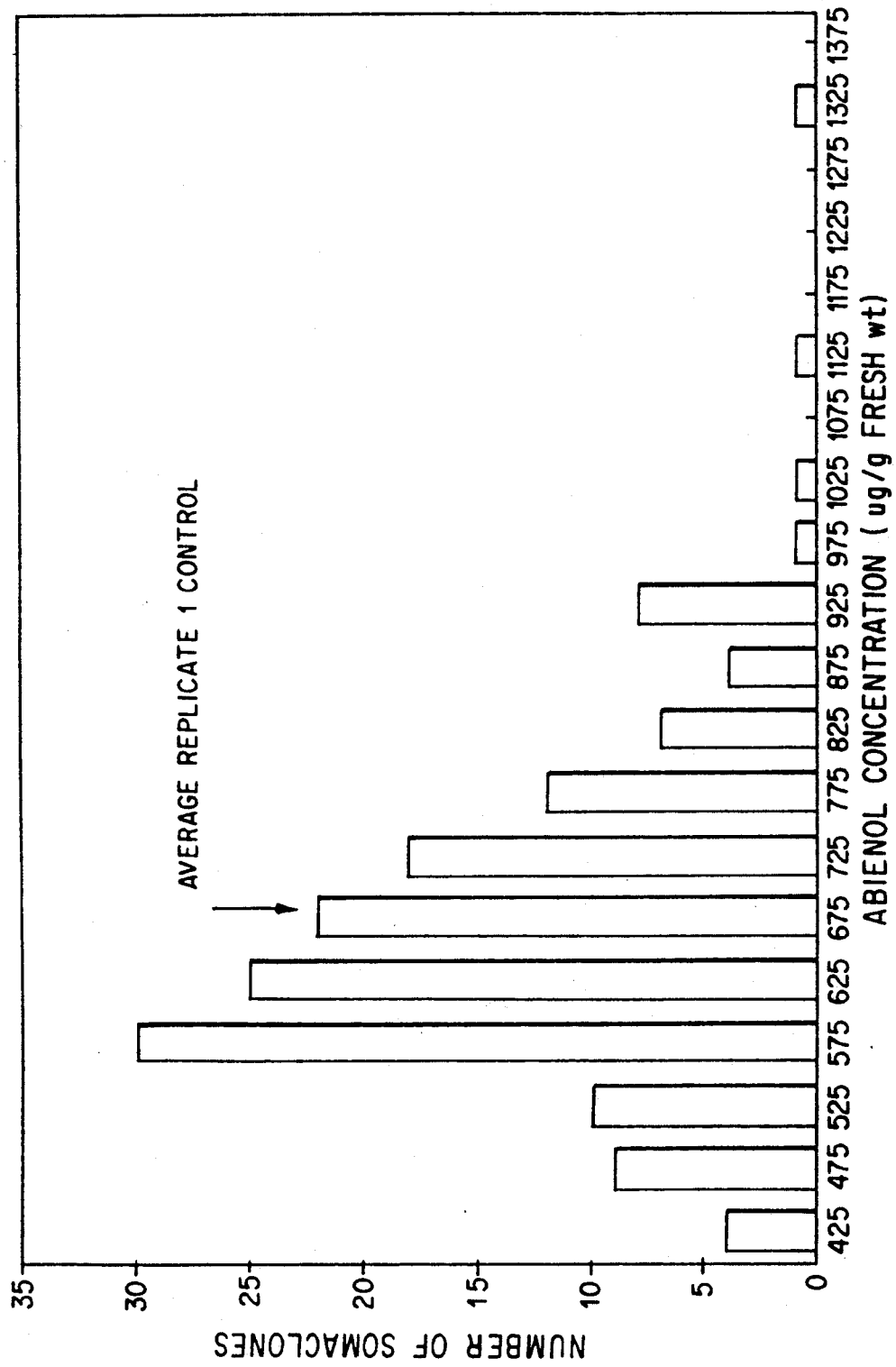
FIGS. 4A and 4B are graphic depictions of the R2 somaclones analyzed for abienol content.
Figure 4B:
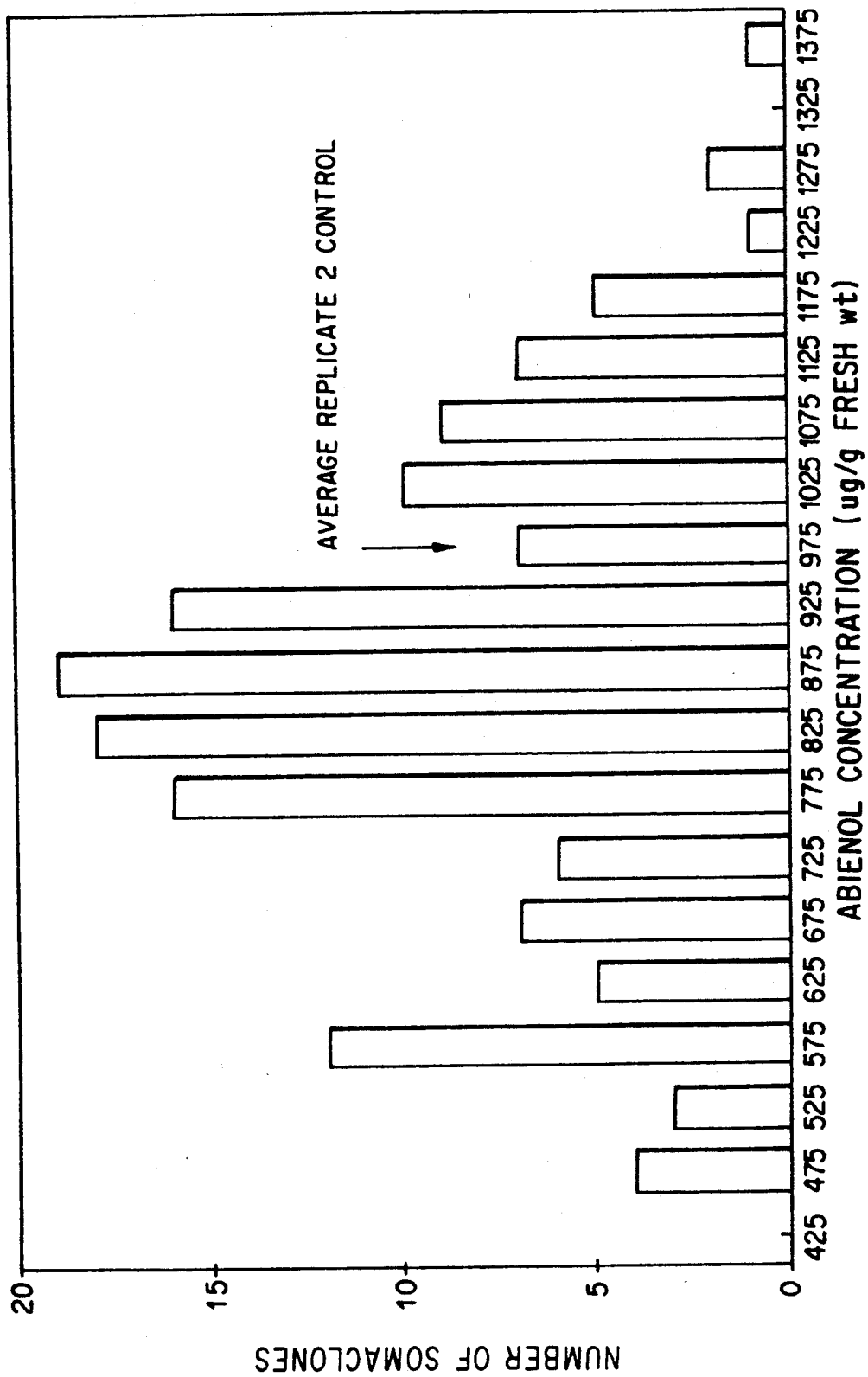

FIG. 4B shows the distribution of abienol from R2 somaclones upon bulk analysis of replicate 2. R2 somaclones represent the second generation of plants. Replicate 1 and replicate 2 differ only in that replicate 2 was harvested much closer to the peak harvest date than replicate 1.

5. DETAILED DESCRIPTION OF THE INVENTION

5.1. Obtaining Somaclonal Variants

As noted above, somaclonal variation can be induced by placing a tissue explant into an appropriate growth medium. In the present case, the tissue is preferably derived from any young tissue of the plant, particularly young leaf tissue. By "young" in the present context is meant tissue from a preflowering plant. Sterilization of the selected tissue is usually performed prior to culture to prevent growth of contaminating microorganisms. Tissue may be immersed in a dilute solution of sodium hypochlorite (e.g. Clorox) for about ten minutes and thereafter rinsed two or three times with sterile distilled water. Other methods of sterilization will also be recognized by those skilled in the art.

A number of nutrient media suitable for plant tissue culture, each containing a distinctive composition of carbon source, salts, minerals and vitamins, are known in the art. Among those which are suitable as the basal medium are B5 (Gamborg et al., *Exp. Cell Res.* 50:151-158, 1968), White's (White, *A Handbook of Plant and Animal Tissue Culture*, Jaques Cattel Press, Lancaster, PA, 1963) and SH (Schenk and Hildebrandt, *Can. J. Bot.* 56:166-204, 1962). Preferred for the culture procedure, however, is MS medium (Murashige and Skoog, *Physiol. Plant.* 15:473-497, 1962).

Variation in the regenerated plants is induced by the presence of a particular hormonal composition in the medium. It has been discovered that the presence of a relatively high concentration of at least one cytokinin will be effective in inducing variation. Among known cytokinins are 6-benzyladenine (6-BA), zeatin, kinetin, and 2-isopentyladenine (2-iP). Concentrations of at least about 5 uM of cytokinin are effective in producing variants among regenerated plants; however, the quantity and quality of variants obtained appear to vary with the cytokinin concentration. Variation occurs at a low frequency at concentrations of 5 $\mu$M, and increases with increasing cytokinin concentration. At cytokinin concentrations of 20 uM or more, while frequency of variation is high, the variations observed tend to be detrimental or undesirable. Therefore, the preferred concentration for the production of high sclareol-producing lines is about 5 uM-20 uM, with the most preferred concentration being about 10 uM. The preferred cytokinin is 6-BA.

Although not necessary for induction of variation, it may also be desirable to include an auxin in the growth medium. Variation will occur in a medium containing only effective amounts of a cytokinin, but the quality of regenerated plants is greatly improved by growth on an auxin- and cytokinin-containing medium. Auxins useful in the present method include indole acetic acid (IAA), indole butyric acid (IBA), naphthalene acetic acid (NAA), and 2,4-dichlorophenoxyacetic acid (2,4-D), with IAA being preferred. The presence of an auxin, and particularly IAA, tends to promote shoot formation; this limits the period of undifferentiated growth, and may therefore obviate the problem associated with accumulation of or many undesirable mutations in plantlet progeny. Generally, a concentration of about 1 uM to about 20 uM of auxin is sufficient to ensure a desirable level of plantlet regeneration.

To initiate regeneration, an explant usually no more than a few square centimeters, is excised from the donor plant and placed on a basal medium with an appropriate hormonal concentration. A callus mass, i.e., a mass of undifferentiated tissue, appears at the cut edges in about 5-10 days; within 2-3 weeks, shoots will begin to appear.

Following shoot regeneration, it is usually preferred to transfer the regenerated shoots to a rooting medium. A preferred rooting medium contains one-half strength MS and naphthalene acetic acid (NAA); the use of NAA increases the frequency of successfully rooted plants. When employed, the preferred concentration for NAA is about 2 $\mu$M; however, possible variations in the composition of the rooting medium will be apparent to those skilled in the art. Once regenerated plants have been rooted, they are transferred to pots and grown to maturity.

5.2 SCREENING FOR VARIANTS

Because the variant regenerated plants which contain higher levels of labdanes do not differ phenotypically from normal regenerated plants, the screening for the desired variants must be performed chemically on the regenerated plants. Labdanes are extractable from leaves of the plants with methanol. Once active leaves from each plant are collected, weighed, and extracted, the methanol extracts are dried down, and the labdane fraction obtained by solid phase extraction. Alternatively, the labdane fraction can be extracted by use of methylene chloride as the solvent. This latter method may be preferred, as it extracts virtually all the available abienol in the sample, and also provides a cleaner product, thereby avoiding the necessity for solid phase extraction. On the final product of either method gas chromatography is conveniently performed according to the method of R. F. Severson et al. (*J. Ag. Food Chem.* 38:566) with the minor modifications noted in Example 1, infra. Peak identification can be accomplished by comparison with authentic labdane standards. The concentration of the selected labdane is determined for each somaclone line, and then compared with the concentrations observed in the highest producing non-variant control lines. As noted above, the range of sclareol yield for average, non-somaclone *N. glutinosa* lines is about 300-600 mg/kg. Any line producing 800 or more mg sclareol/kg is considered a variant. Similarly, the range of cis-abienol yield for average, non-somaclone *N. tabacum* lines is about 0-200 mg/kg, with a rare unusual line producing as much as about 700 mg/kg. Therefore, any line producing more than about 800 mg of cis-abienol/kg is considered a variant.

5.2.1. HIGH SCLAREOL-PRODUCING SOMACLONES

Figure 1:
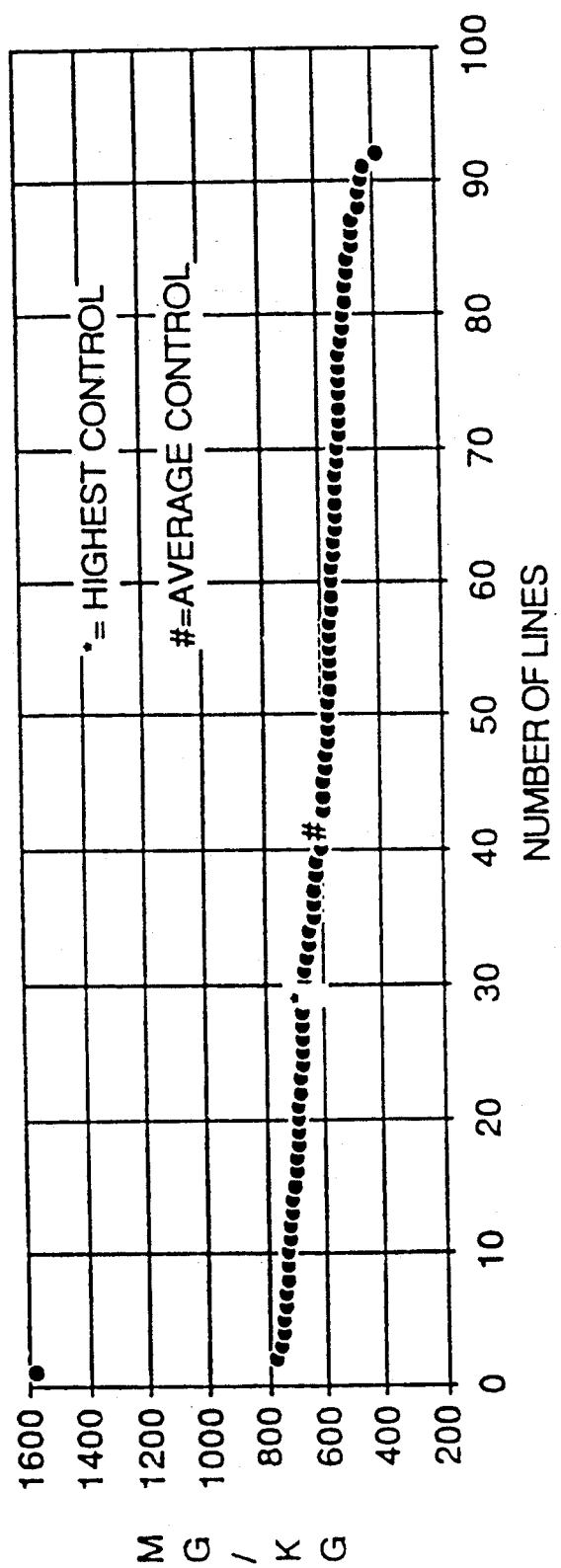

In the present trials, leaf explants from two different genotypes of *N. glutinosa* (designated VS and DE) were cultured and screened for somaclones producing high levels of sclareol. In one line, DE, twenty-six somaclone lines, out of a total of 94, exhibited ranges of sclareol production which were 11-32% over the highest control (see FIG. 1). One line, however, showed a 2.5-fold increase in sclareol (1581 mg/kg) over the highest control. This line, DE-72, also produced 415 mg/kg manool, another labdane; this is approximately a two-fold increase over the highest control. On the other hand, phytol, a non-labdane-alcohol produced by the degradation of chlorophyll was present in amounts similar to those in the controls, indicating that the biochemical and genetic changes that distinguish line 72 involve only the labdane pathway. This is consistent with previous observations on the utility of somaclonal variation for introducing single gene changes into the genome that might regulate an entire biochemical pathway.

Observations on the VS somaclones parallel those seen with DE, with one difference: this genotype is, overall, not as productive as DE for sclareol synthesis, and therefore, VS somaclones do not accumulate sclareol to the level that the DE somaclones do. However, it is worthy of note that a very similar distribution for increased sclareol synthesis (shown in FIG. 2) exists in the VS somaclones when compared to the DE somaclones. Thus, the technique provides a reliable means of obtaining increased labdane production in any given Nicotiana line, and truly outstanding results are obtainable when the starting material is a line already exhibiting sclareol production at the high end of the normal range, i.e., at least about 500-600 mg/kg.

It will be recognized by those skilled in the art that the figures given from average sclareol production by the modified lines of the present invention, and the control line as well, refer to production observed under substantially ideal growing conditions for *Nicotiana glutinosa*, in one season's production. Clearly, environmental conditions have the potential of affecting overall yield of the plant, as well as production of sclareol itself. It is within the skill of the experienced artisan to design a planting strategy which will optimize yield of sclareol under the environmental conditions of the region where the plants are to be grown. Generally, however, traditional tobacco agronomy is applicable to growth of *N. glutinosa*. It has been determined that optimum sclareol synthesis occurs at the onset of flowering, and that almost 70% of sclareol production occurs in the top two thirds of the plant. Therefore, by harvesting the top two thirds of the plants after flowering has occurred, optimal sclareol levels can be obtained, and enough plant material will be left in the ground to ensure good secondary growth that will permit a second harvest from the same plot of land. All yield/acre figures presented herein represent the results of two harvests.

The present method has been used to repeatedly produce high labdane-producing lines of *Nicotiana glutinosa*. Seed of a particularly high sclareol producing line has been deposited with the American Type Culture Collection, under Accession Number 40463. The scope of the present invention is not limited, however, solely to the somaclonal variant lines per se, nor to a single deposited line. The present invention also encompasses all hybrids, both inter- and intraspecific, mutants, somaclones, and gametoclones, derived from the original somaclonal variants, which retain the identifying characteristic of high sclareol production.

The availability of such *Nicotiana glutinosa* variants provides a novel method by which sclareol may be produced on a commercial scale. Although the production of sclareol by *Nicotiana glutinosa* has previously been known, this plant has never been exploited for this purpose, presumably because the natural yield of this plant is quite low. The present availability of high-yielding somaclones, however, has now provided a means by which sclareol can be produced in commercially feasible quantities. Thus, the present somaclones represent an improvement in methods for obtaining sclareol from plant sources, by extraction of sclareol from leaves and other plant parts of the novel somaclones of *N. glutinosa*, having a sclareol content of at least 800 mg/kg of fresh plant weight.

5.2.2. HIGH CIS-ABIENOL PRODUCING SOMACLONES

Similar success has been achieved using *N. tabacum* as a source for increased abienol production. The variety Ti-1396 was employed as the source for tissue explants for somaclonal variation; the selection of the source variety was made after screening a number of varieties to determine which was the best abienol producer within the normal range of abienol production for *N. tabacum*. Table I shows the relative yield of abienol among three lines, over three harvests.

TABLE I

| Line | Harvest | Leaves | (%) | Stems | (%) | Total | Biomass/Acre | Abienol/Acre |
|---|---|---|---|---|---|---|---|---|
| Ti-1396 | 7/29 | 0.56 | 47 | 0.62 | 53 | 1.18 | 4.72 | 1.75 |
|  | 8/21 | 0.90 | 41 | 1.30 | 59 | 2.20 | 8.80 | 3.36 |
|  | 10/8 | 1.26 | 40 | 1.87 | 60 | 3.13 | 12.50 | 2.13 |
| Gen 911 | 7/29 | 0.28 | 38 | 0.45 | 62 | 0.73 | 2.92 | 0.39 |
|  | 8/21 | 0.66 | 32 | 1.39 | 68 | 2.05 | 8.20 | 0.84 |
|  | 10/8 | 0.79 | 27 | 2.09 | 73 | 2.88 | 11.52 | 0.61 |
| Magnolia | 7/29 | 0.71 | 49 | 0.75 | 51 | 1.46 | 5.84 | 1.55 |
|  | 8/21 | 0.75 | 38 | 1.21 | 62 | 1.96 | 7.84 | 0.71 |
|  | 10/8 | 0.81 | 34 | 1.59 | 66 | 2.40 | 9.60 | 1.47 |

Leaf and stem weights are given in Kg. Biomass/acre values are Kg biomass calculated for one acre and abienol/acre values are in Kg abienol/acre.

Following the procedure outlined below in Example 1, over 200 somaclones ($R_o$) were regenerated, transplanted to soil, and transferred to the greenhouse. The somaclones were allowed to grow until flowering, and then leaves were removed for laboratory analysis. A significant amount of variation for abienol synthesis was observed among the somaclone lines, with levels ranging from 0 to up to almost 1000 mg/kg of leaf material. In this planting, the control plants averaged in the range of 400-450 mg/kg of leaf material. A graphic depiction of the variation observed in the $R_1$ generation of these somaclones is presented in FIG. 1. Although not all lines produced from somaclones reached even control levels, a number significantly outperformed the control lines, producing about 1.5-2.0 times the amount of abienol. The results of these trials, showing the best somaclone lines based on two harvests, are summarized in Table II. Equally important is the fact that the increase in abienol production does not appear to have any adverse effect on the viability or yield of the improved plants; Table II also shows that the biomass yield of somaclones was essentially the same for somaclones as for control lines.

TABLE II

Selected Ti-1396 Somaclone Lines

| Somaclone | Abienol (mg/Kg) | | Biomass (Kg/plant) |
|---|---|---|---|
| | Harvest 1 | Harvest 2 | |
| 169 | 979.0 | 349.0 | 2.32 |
| 19 | 866.2 | 318.0 | 2.55 |
| 128 | 776.9 | 339.6 | 2.91 |
| 103 | 764.3 | 489.5 | 2.27 |
| 179 | 756.3 | 301.0 | 2.64 |
| 193 | 749.7 | 280.0 | 1.73 |
| 199 | 748.6 | 370.0 | 3.32 |
| 164 | 699.5 | 323.0 | 2.36 |
| 44 | 687.0 | 493.7 | 2.82 |
| 43 | 686.7 | 618.2 | 3.36 |
| 90 | 674.3 | 352.0 | 2.18 |
| 28 | 650.8 | 317.3 | 2.36 |
| 122 | 638.5 | 278.0 | 2.41 |
| 62 | 637.5 | 336.0 | 3.09 |
| 148 | 623.8 | 274.0 | 2.27 |
| 54 | 615.9 | 326.0 | 2.27 |
| 109 | 595.6 | — | 2.68 |
| 111 | 294.0 | 636.0 | 2.64 |
| Control (average) | 447.0 | 297.8 | 2.42 |

It will be understood that the defining features of the somaclone lines claimed herein are based on average abienol production under substantially ideal growing conditions for tobacco, in one growing season. Adverse environmental conditions have the potential for affecting the overall yield of the plants as well as production of abienol itself. It is within the skill of the experienced artisan to design a planting strategy which will optimize the yield of abienol under the environmental conditions under which the plant is to be grown. However, the somaclones do not require growing conditions different from those required for the parent plant, and therefore, as a general rule, traditional tobacco agronomy will apply to growing of the present N. tabacum somaclones. Harvest may be once, or more than once, during the growing season, since an initial harvest frequently results in growth of new vertical stalks with full leaves and flowers. Peak abienol production occurs at the time of flowering. Further, daily fluctuations in abienol production occurs, so that harvesting should preferably be undertaken in mid- to late afternoon, to maximize abienol yield. The initial harvest should be followed by an additional application of fertilizer, in order to aid in boosting the abienol content of the second harvest. It will also be noted that heavy rainfall can cause a temporary drop in abienol content, which content will gradually return to normal within a 10-day period. Although abienol is primarily produced on the leaves of the plant, it is obtainable from virtually all parts of the plant, and the figures provided here reflect the use of the entire plant.

Seed of one of the somaclones of the present invention, the line designated as 96-169, have been deposited with the American Type Culture Collection, under accession number 40462. The deposit is merely exemplary, however, and is not intended to limit the scope of the present claims to either the somaclone line per se or a single deposited line. It will be readily seen, by reference to Table II, that many plants within the scope of the present claims can routinely be produced. The invention also encompasses hybrids, both inter- and intraspecific, produced using the plants of the present invention as one or both parents, as well as clones, somaclones, gametoclones, and mutants of the claimed lines, which retain the identifying characteristic of high abienol production. Other somaclones of high-yielding tobacco lines are also obtainable using the methods described in the present application.

The availability of the present high yielding N. tabacum lines provides a method by which cis-abienol may be produced on a commercial scale. Although the production of abienol by N. tabacum has previously been known, tobacco has not previously been exploited for this purpose, presumably because of the normally relatively low yield. Thus, the present somaclones represent an improvement in methods for obtaining abienol, by extraction from leaves and other plant parts of the novel N. tabacum somaclones.

The following non-limiting examples will more clearly illustrate the plant lines and methods of the present invention.

6. EXAMPLES

6.1. Inducing Somaclonal Variation

The following example illustrates conditions under which somaclonal variants of Nicotiana sp. producing higher than normal amounts of labdanes have been repeatedly produced:

Young, fully expanded leaves of Nicotiana glutinosa or Nicotiana tabacum are isolated from donor plants and surface sterilized. Sterilization for greenhouse grown plants is usually conducted for about 6 minutes in 8% commercial bleach (0.42% sodium hypochlorite). The bleach is rinsed off in three changes of sterile distilled water.

The leaf is cut into 1-5 cm² sections, and transferred aseptically to a jar containing solid MS medium (Murashige and Skoog, Physiol. Plant. 15:473-479, 1962) with the addition of 6-BA at a concentration of about 10 μM, and IAA at a concentration of about 10 μM. A callus mass develops in about 5-10 days, and shoots are regenerated in 2-3 weeks. All shoots regenerated from callus are transferred to a rooting medium comprising MS medium with 2 μM NAA. Plantlets are recovered on rooting medium from 8-10 weeks after culture initiation. Between 2-10 plants are typically obtained from each explant that regenerated shoots.

Over 200 regenerated plants ($R_o$) were obtained from each group; these were placed in soil and transferred to a greenhouse. The $R_o$ plants are self-fertilized, and seed are collected from each regenerated plant to evaluate the next ($R_1$) generation. Seeds for $R_1$ plants were sown in the greenhouse and were transplanted to the replicated field plots to evaluate genetic variability.

6.2. SCREENING FOR LABDANE PRODUCTION

The following procedures illustrate the method of testing for sclareol content in leaves of $R_1$ lines.

Methanol extraction is preferably performed on leaves from the top third of the plant. The leaves are randomized, and then several leaf disks are generated therefrom with a 1.5 cm cork borer, excluding the midvein of the leaf. 10 grams of leaf disks are weighed out and placed in a 250 ml beaker or extraction flask. 100 ml of reagent grade methanol is added to each flask and shaker on a rotary shaker for 8-10 hours at 160 rpm. The solvent is decanted and saved. A fresh 100 ml aliquot of methanol is then added, and shaken for 2 hours. The solvent is decanted and combined with the first reserved solvent fractions.

Drying down of methanol can be achieved in a number of different ways. In a situation in which large numbers of samples are being prepared, drying time can be accomplished by evaporation in a laminar flow hood for 1-2 days. When a small number of samples are being evaluated, the methanol can be evaporated by bubbling nitrogen gas through the methanol for 2-3 hours.

After drying, the residue is dissolved in two 5 ml aliquots of hexane:methylene chloride (1:1), and adding 2.0 ml distilled water to the second 5 ml aliquot to dissolve the water soluble components of the residue. In a 15 ml conical centrifuge tube, 0.5 ml of a 5 mg/ml solution of 1-heptadecanol (internal standard) is combined with the dissolved residue, and the phases allowed to separate. If necessary the volume can be brought up to 10 ml with additional hexane:methylene chloride.

A solid phase extraction column (silica gel, 500 mg adsorbant, 3 ml capacity) is set up and conditioned with 2 ml hexane:methylene chloride. From the top phase of the sample, 1 ml is removed and loaded onto the column. The sample is washed onto the column with 2 ml of hexane:methylene chloride. The column is eluted with $4 \times 0.5$ ml aliquots of acetone, and the eluate collected in 0.5 dram vials. The eluant is evaporated with nitrogen gas, and the residue redissolved with 1 ml ethyl acetate. The sample is then read for injection into a gas chromatograph.

Chromatography is conducted according to the method of Severson et al., supra, with the following modifications:

| | |
|---|---|
| Split ratio | 200:1 |
| Column | 25M × .22 mm ID CP-SIL 5CB (CHROMOPAK) |
| Temperature program | 160° C. isothermal (9 minutes) 5° C./minute to 295° C., and hold for 4 minutes |
| Run time | 40 minutes |
| Injection | 1 μl |
| Additional specifications include: | |
| He | 30 ml/min |
| $H_2$ | 30 ml/min |
| Air | 400 ml/min |
| Column Flow | 0.99 ml/min |
| Injection Temperature | 250° C. |
| Detection Temperature | 300° C. |

In this manner, over 200 regenerated plants from each of the VS and DE lines were tested for amount of sclareol production. The results are presented in FIGS. 1 and 2.

In this manner, $R_1$ generation plants developed from Ti-1396 were screened for abienol production. A summary of the selected lines provided in Table II, and FIG. 1 indicates the distribution of abienol production over the entire generation. Further trials with abienol-producing variants are discussed in the following sections.

6.3. $R_2$ GENERATION

Figure 2:
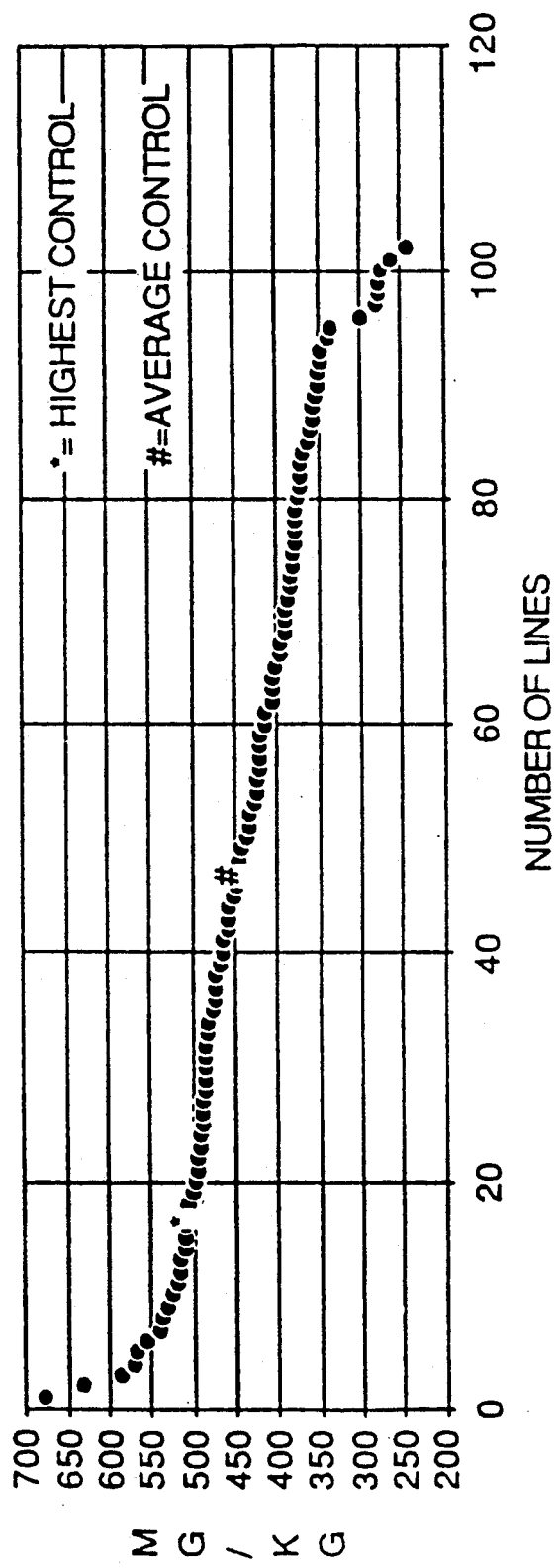
Figure 3:
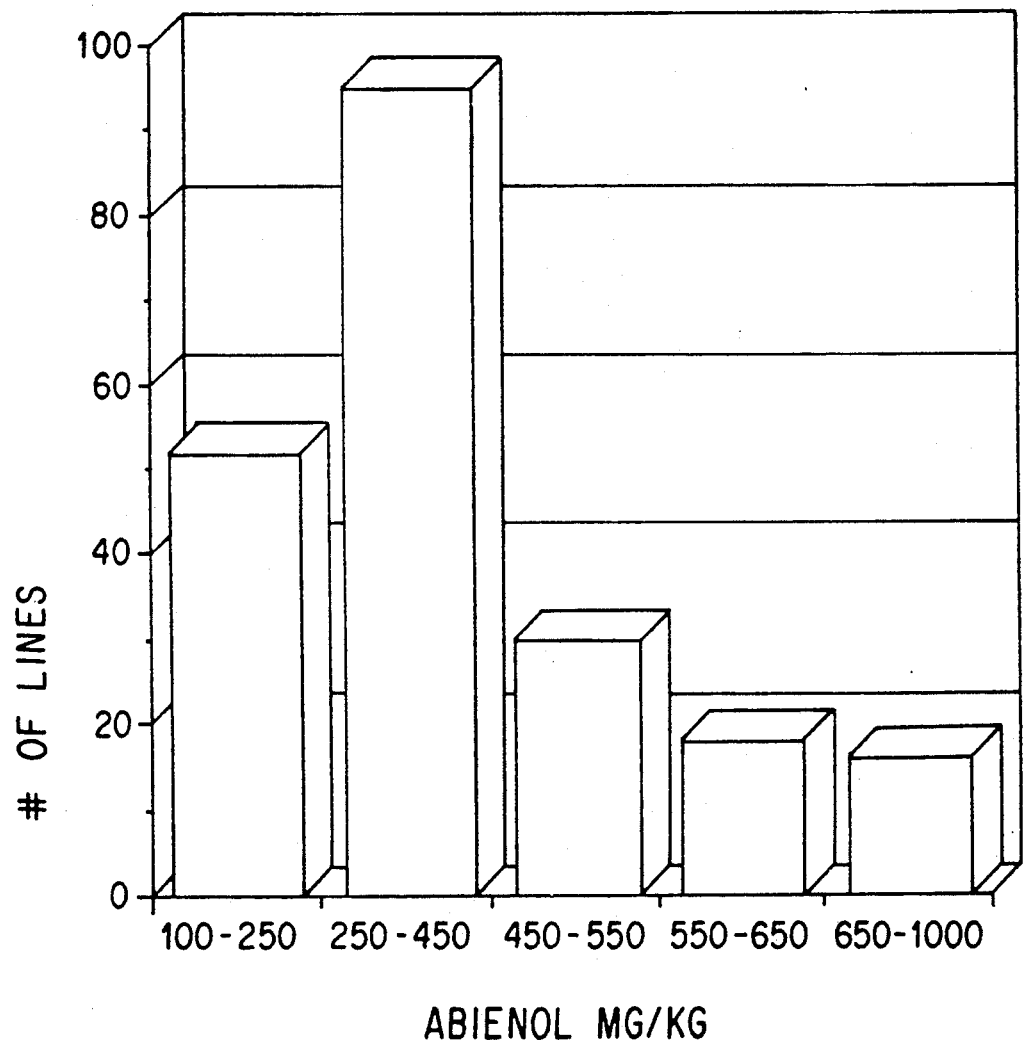
FIG. 3 is a graphic depiction of the pattern of variation among the $R_1$ somaclones obtained from the variety T1-1396 which was subjected to a treatment of somaclonal variation. The average control value obtained for wild type *Nicotiana tabacum* was 400-450 mg abienol/kg leaves)

An $R_2$ generation of the high abienol producing variants was also evaluated under field conditions. Due to the genetic complexity of abienol synthesis, an expected amount of genetic segregation was observed. The results shown in Table III, however, show that top performing $R_1$ somaclones continued to produce high levels of abienol. Note, for example, DNAP-62 and DNAP-179, which were among the better $R_1$ somaclones in terms of abienol synthesis. The difference observed between replicate 1 and replicate 2 in both controls and somaclones can be attributed to the time interval between harvest and analysis of replicate 1 and replicate 2. Replicate 2 was harvested much closer to the peak harvest date, and therefore would be expected to demonstrate higher abienol concentrations. Overall, however, the $R_2$ somaclones outperformed the Ti-1396 controls in both replicates, as seen in FIG. 2. A significant number of somaclones exceeded the mean abienol concentration for the Ti-1396 control in both replicates.

6.4. SOMACLONE HYBRIDS

An effort was also made to intercross high abienol-producing somaclones, and to evaluate $F_1$ hybrids for improved abienol production. $R_1$ seed from the top 10 somaclone lines was sown in the greenhouse, and the plants were then screened and the highest yielding plant selected for intercrossing. All crosses and their reciprocals were made in the greenhouse from January to March (Table IV). A total of 71 crosses were made, and $F_1$ seed collected and sown for field evaluation. The $F_1$'s were planted in replicated plots of 15 plants/plot, with two types of control. Ti-1396 was used as one control and planted at a frequency of one Ti-1396 control plot (15 plants) per five $F_1$ hybrid plots. The other set of controls were the selfed parental somaclones. Abienol was tested throughout the growing season, and samples harvested in early September. Analysis was based on a sampling protocol in which one leaf was removed from the top ⅓ of 10 different plants/plot, wrapped in a larger leaf and placed in a paper bag. The chemical analysis was as outlined above.

The resulting hybrid lines revealed a broad range of abienol production, with some of the $F_1$ hybrid lines producing abienol levels higher than either parent or Ti-1396 control while others exhibited abienol levels higher than the Ti-1396 control but equal to both parental types. The dramatic increase in some hybrids is probably a reflection of a genetically complementary combination between two somaclones.

The top 20% (15 lines) of abienol producing $F_1$ hybrid lines were selected by comparing the abienol levels found within these lines to those found in both the nearest Ti-1396 control plot and the corresponding parental plots. In each of the selected hybrids, the concentration of abienol found in the $F_1$ hybrid line was significantly greater than the average concentration of the abienol found in the nearest Ti-1396 control plots. The majority of hybrid combinations selected exhibited abienol levels much higher than either parental type. A summary of the observations on the top hybrid lines is presented in Table V. Thus, intercrossing of the top abienol-producing somaclones represents a valuable technique for increasing overall abienol synthesis.

TABLE III

| Somaclone Number[a] | R₂ Somaclone = Bulk Analysis | |
|---|---|---|
| | Replicate 1 | Replicate 2 |
| 6-19-1 | 501 | 1170 |
| 6-19-2 | 643 | 1019 |
| 6-19-3 | 934 | 887 |
| 6-19-4 | 578 | 917 |
| 6-19-5 | 912 | 1117 |
| 6-19-6 | 759 | 931 |
| 6-19-7 | 437 | 933 |
| 6-19-8 | 596 | 456 |
| 6-19-9 | 564 | 936 |
| 6-19-10 | 690 | 951 |
| 6-19-11 | 523 | 901 |
| 6-19-12 | 610 | 653 |
| 6-19-13 | 641 | 805 |
| 6-19-14 | 812 | 1097 |
| 6-19-15 | 793 | 1168 |
| Average | 666 | 929 |
| 6-43-1 | 622 | 1270 |
| 6-43-2 | 642 | 859 |
| 6-43-3 | 627 | 802 |
| 6-43-4 | 652 | 812 |
| 6-43-5 | 945 | 865 |
| 6-43-6 | 562 | 660 |
| 6-43-7 | 634 | 595 |
| 6-43-8 | 553 | 1061 |
| 6-43-9 | 669 | 901 |
| 6-43-10 | 689 | 1191 |
| 6-43-11 | 646 | 870 |
| 6-43-12 | 650 | 1128 |
| 6-43-13 | 717 | 941 |
| 6-43-14 | 907 | 753 |
| 6-43-15 | 596 | 1195 |
| Average | 674 | 927 |
| 6-44-1 | 684 | 1024 |
| 6-44-2 | 991 | 1126 |
| 6-44-3 | 531 | 505 |
| 6-44-4 | 613 | 983 |
| 6-44-5 | 695 | 919 |
| 6-44-6 | 721 | 712 |
| 6-44-7 | 630 | 859 |
| 6-44-8 | 751 | 863 |
| 6-44-9 | 571 | 1051 |
| 6-44-10 | 544 | 789 |
| 6-44-11 | 747 | 1040 |
| 6-44-12 | 637 | — |
| 6-44-13 | 615 | 950 |
| 6-44-14 | 647 | 1011 |
| 6-44-15 | 731 | 636 |
| Average | 674 | 891 |
| 6-62-1 | 912 | 1123 |
| 6-62-2 | 760 | 1090 |
| 6-62-3 | 932 | 443 |
| 6-62-4 | 827 | 884 |
| 6-62-5 | 690 | 1043 |
| 6-62-6 | 710 | 892 |
| 6-62-7 | 724 | 931 |
| 6-62-8 | 1100 | 832 |
| 6-62-9 | 797 | 1121 |
| 6-62-10 | 686 | 555 |
| 6-62-11 | 635 | 1631 |
| 6-62-12 | 582 | 863 |
| 6-62-13 | 466 | 827 |
| 6-62-14 | 675 | 838 |
| 6-62-15 | 1022 | 597 |
| Average | 768 | 911 |
| 6-90-1 | 696 | 1042 |
| 6-90-2 | 420 | 772 |
| 6-90-3 | 811 | 1060 |
| 6-90-4 | 724 | 735 |
| 6-90-5 | 698 | 596 |
| 6-90-6 | 523 | 533 |
| 6-90-7 | 560 | 705 |
| 6-90-8 | 632 | 865 |
| 6-90-9 | 619 | 765 |
| 6-90-10 | 863 | 1197 |
| 6-90-11 | 903 | 756 |

TABLE III-continued

| Somaclone Number[a] | R₂ Somaclone = Bulk Analysis | |
|---|---|---|
| | Replicate 1 | Replicate 2 |
| 6-90-12 | 643 | 1073 |
| 6-90-13 | 712 | 556 |
| 6-90-14 | 883 | 897 |
| 6-90-15 | 712 | 782 |
| Average | 693 | 822 |
| 6-103-1 | 903 | 751 |
| 6-103-2 | 609 | 729 |
| 6-103-3 | 792 | 1059 |
| 6-103-4 | 720 | 1004 |
| 6-103-5 | 566 | 1066 |
| 6-103-6 | 702 | 706 |
| 6-103-7 | 797 | 942 |
| 6-103-8 | 633 | 989 |
| 6-103-9 | 815 | 954 |
| 6-103-10 | 620 | 893 |
| 6-103-11 | 708 | 1230 |
| 6-103-12 | 798 | 914 |
| 6-103-13 | 744 | 877 |
| 6-103-14 | 828 | 1004 |
| 6-103-15 | 697 | 795 |
| Average | 729 | 927 |
| 6-128-1 | 552 | 784 |
| 6-128-2 | 486 | 756 |
| 6-128-3 | 683 | 549 |
| 6-128-4 | 551 | 980 |
| 6-128-5 | 464 | 562 |
| 6-128-6 | 588 | 1054 |
| 6-128-7 | 444 | 801 |
| 6-128-8 | 811 | 805 |
| 6-128-9 | 707 | 847 |
| 6-128-10 | 665 | 1124 |
| 6-128-11 | 612 | 1029 |
| 6-128-12 | 596 | 796 |
| 6-128-13 | 686 | 856 |
| 6-128-14 | 833 | 933 |
| 6-128-15 | 486 | 815 |
| AVERAGE | 611 | 846 |
| 6-164-1 | 435 | 643 |
| 6-164-2 | 627 | 579 |
| 6-164-3 | 579 | 814 |
| 6-164-4 | 682 | 575 |
| 6-164-5 | 870 | 846 |
| 6-164-6 | 798 | 571 |
| 6-164-7 | 723 | 662 |
| 6-164-8 | 749 | 946 |
| 6-164-9 | 555 | — |
| 6-164-10 | 762 | 788 |
| 6-164-11 | 684 | 573 |
| 6-164-12 | 715 | 676 |
| 6-164-13 | 565 | 695 |
| 6-164-14 | 593 | 499 |
| 6-164-15 | 546 | 697 |
| AVERAGE | 659 | 683 |
| 6-169-1 | 580 | 580 |
| 6-169-2 | 650 | 826 |
| 6-169-3 | 577 | 1111 |
| 6-169-4 | 694 | 834 |
| 6-169-5 | 566 | 644 |
| 6-169-6 | 517 | 978 |
| 6-169-7 | 535 | 873 |
| 6-169-8 | 618 | 855 |
| 6-169-9 | 464 | 934 |
| 6-169-10 | 594 | 498 |
| 6-169-11 | 737 | 911 |
| 6-169-12 | 525 | 733 |
| 6-169-13 | 696 | 1034 |
| 6-169-14 | 783 | 635 |
| 6-169-15 | 578 | 610 |
| AVERAGE | 608 | 804 |
| 6-179-1 | 678 | 830 |
| 6-179-2 | 895 | 787 |
| 6-179-3 | 581 | 870 |
| 6-179-4 | 578 | 908 |
| 6-179-5 | 490 | 851 |
| 6-179-6 | 421 | 758 |
| 6-179-7 | 566 | 1257 |
| 6-179-8 | 477 | 696 |
| 6-179-9 | 688 | 867 |

TABLE III-continued

R₂ Somaclone = Bulk Analysis

| Somaclone Number[a] | Replicate 1 | Replicate 2 |
|---|---|---|
| 6-179-10 | 465 | 804 |
| 6-179-11 | 505 | 800 |
| 6-179-12 | 1450 | 576 |
| 6-179-13 | 763 | 761 |
| 6-179-14 | 571 | 818 |
| 6-179-15 | 577 | 760 |
| AVERAGE | 647 | 823 |

[a] R₂ seed was collected from top 10 R₁ somaclones in 1987 by individual plants (see FIG. 7). Each line had 15 plants, therefore 6-19-1 refers to a somaclone of TI-1396, somaclone 19, R₁ plant number 1, 30 plants of this single plant selection were planted in 1988 (2 replications). The data shown here are from bulk analysis (see Methods).

TABLE V

Top Abienol Producing F1 Hybrid Lines

| F₁ Hybrid Cross | [Abienol] | Nearest Controls [Abienol] | Difference [Abienol] (F1 hybrid-Control) | Parental Somaclone line | [Abienol] |
|---|---|---|---|---|---|
| 128-2 × 44-2 | 1208 | 577 | +631 | 128-2 | 325 |
| | | | | 44-2 | 670 |
| 128-2 × 62-1 | 1131 | 519.5 | +611.5 | 128-2 | 325 |
| | | | | 62-1 | 490 |
| 44-2 × 90-2 | 1037 | 513 | +524 | 44-2 | 670 |
| | | | | 90-2 | 314 |
| 179-1 × 103-1 | 982 | 577 | +405 | 179-1 | 260 |
| | | | | 103-1 | 676 |
| 128-2 × 169-2 | 960 | 207 | +753 | 128-2 | 325 |
| | | | | 169-2 | 227 |
| 90-2 × 44-2 | 865 | 577 | +288 | 90-2 | 314 |
| | | | | 44-2 | 670 |
| 128-2 × 103-1 | 840 | 588 | +252 | 128-2 | 325 |
| | | | | 103-1 | 676 |
| 62-1 × 128-2 | 769 | 434.5 | +334.5 | 62-1 | 490 |
| | | | | 128-2 | 325 |
| 128-2 × 179-1 | 748 | 397.7 | +350.3 | 128-2 | 325 |
| 103-1 × 169-2 | 702 | 478 | +224 | 103-1 | 676 |
| | | | | 169-2 | 227 |
| 103-1 × 62-1 | 673 | 588 | +85 | 103-1 | 676 |
| | | | | 62-1 | 490 |
| 62-1 × 179-1 | 667 | 432.7 | +234.3 | 62-1 | 490 |
| | | | | 179-1 | 260 |
| 19-2 × 44-2 | 645 | 269.3 | +375.7 | 19-2 | 639 |
| | | | | 44-2 | 670 |
| 164-1 × 44-2 | 641 | 222.5 | +418.5 | 164-1 | 437 |
| | | | | 44-2 | 670 |
| 169-2 × 62-1 | 627 | 478 | +149 | 169-2 | 227 |
| | | | | 62-1 | 490 |

All abienol concentrations in mg abienol/g fresh leaf.

TABLE IV

Ti-1396 Somaclonal F₁ Hybrids

| Female | Male | | | | | | | | | |
|---|---|---|---|---|---|---|---|---|---|---|
| | 169-2 | 19-2 | 128-2 | 103-1 | 179-1 | 164-1 | 44-2 | 43-2* | 90-2 | 62-1 |
| 169-2 | S | — | S | S | S | — | — | — | S | S |
| 19-2 | S | S | S | S | S | S | S | — | S | — |
| 128-2 | S | S | S | S | S | S | S | — | — | S |
| 103-1 | S | S | S | S | S | — | — | — | S | S |
| 179-1 | S | S | S | S | S | S | — | — | S | S |
| 164-1 | S | — | S | S | S | S | S | — | S | S |
| 44-2 | S | S | S | S | S | S | S | — | S | S |
| *43-2 | — | — | — | — | — | — | — | — | — | — |
| 90-2 | S | S | S | — | S | S | S | — | S | S |
| 62-1 | S | S | S | S | S | S | S | — | S | S |

*Plant 43-2 was removed from intercrossing program due to exhibition of tobacco mosaic virus (TMV) symptoms
S = Seed collected and sown from this cross.
— = No seed collected

What is claimed is:

1. A Nicotiana tabacum plant which produces at least about 800 mg of cis-abienol per kg of fresh plant weight per growing season and derivatives thereof which produce at least about 800 mg of cis-abienol per kg of fresh weight per growing season.

2. The plant of claim 1 which produces at least about 1000 mg/kg of cis-abienol and derivatives thereof which produce at least about 1000 mg/kg of cis-abienol.

3. The plant of claim 1 which produces at least about 1200 mg/kg of cis-abienol and derivatives thereof which produce at least about 1200 mg/kg of cis-abienol.

4. The plant of claim 1 which produces at least about 1600 mg/kg of cis-abienol and derivatives thereof which produce at least about 1600 mg/kg of cis-abienol.

5. The plant of claim 1, 2, 3 or 4 which is a hybrid.

6. A variant Nicotiana tabacum plant which is derived from seed deposited with the American Type Culture Collection under accession number ATCC 40462 and derivatives thereof which produce at least about 800 mg of cis-abienol per kg of fresh plant weight per growing season.

7. Seed of the plant of claim 1.

8. Seed of the plant of claim 2.
9. Seed of the plant of claim 3.
10. Seed of the plant of claim 4.
11. Seed of the plant of claim 5.
12. Seed of the plant of claim 6.
13. A leaf of the plant of claim 1.
14. A leaf of the plant of claim 2.
15. A leaf of the plant of claim 3.
16. A leaf of the plant of claim 4.
17. A leaf of the plant of claim 5.
18. A leaf of the plant of claim 6.
19. The plant of claim 1, 2, 3 or 4 which is a somaclonal variant.

* * * * *